(12) United States Patent
Weiner et al.

(10) Patent No.: US 6,332,897 B1
(45) Date of Patent: Dec. 25, 2001

(54) ASSAY METHODS

(75) Inventors: Michael Phillip Weiner; Richard Gordon Buckholz, both of Cary, NC (US)

(73) Assignee: Glaxo Wellcome Inc., Research Triangle Park, NC (US)

( * ) Notice: Subject to any disclaimer, the term of this patent is extended or adjusted under 35 U.S.C. 154(b) by 0 days.

(21) Appl. No.: 09/049,325

(22) Filed: Mar. 27, 1998

(51) Int. Cl.[7] .............................. C12Q 1/68; C12N 15/64
(52) U.S. Cl. ................................. 735/6; 435/91.4
(58) Field of Search ......................... 435/6, 91.4, 254.21, 435/320.1

(56) References Cited

U.S. PATENT DOCUMENTS 5,283,173 * 2/1994 Fields et al. .............................. 435/6

FOREIGN PATENT DOCUMENTS

94/10300 * 5/1994 (WO) .
97/47763 * 12/1997 (WO) .

OTHER PUBLICATIONS

Finley, Jr. et al. (1997) Two–hybrid analysis of genetic regulatory networks. In: The Yeast Two–Hybrid System. Bartel, P.L., Fields, S. (Eds.) Oxford University Press, New York, N.Y., pp. 197–214.*

* cited by examiner

*Primary Examiner*—Robert A. Schwartzman
(74) *Attorney, Agent, or Firm*—Karen L. Prus (57) ABSTRACT

The present invention relates to an automated format for the yeast two hybrid assay for protein-protein interactions.

10 Claims, 7 Drawing Sheets

Translation of the T7 Controlling elements (T7CE)

```
T7 PROMOTER->                        RBS            fMet...MCS
TTAATACGACTCACTATAGGGAGACCAAAGAAGGAGATATACATCATG...
LeuIleArgLeuThrIleGlyArgProLysLysGluIleTyrIleMet...
```

Clone random 500 bp cDNA fragments,
Transform T7RNAP+, Sup+ E.coli,
Screen plaques Phage Display
in E.coli,

FIG. 7B

Transform T7RNAP−, Sup+ E.coli,
Transform M13 into Sup− yeast

Y2H
in Yeast

FIG. 7C

ASSAY METHODS

FIELD OF THE INVENTION

The present invention relates to methods useful for detecting protein-protein interactions. Protein-protein interactions enable the association of two or more proteins through the formation of non-covalent bonds when two protein surfaces are precisely matched. These bonds account for the specificity of recognition. Protein-protein interactions are involved, for example, in the assembly of enzyme subunits; in antigen-antibody reactions; in forming the supramolecular structures of ribosomes, filaments, and viruses; in transport; and in the interaction of receptors on a cell with growth factors and hormones. Products of oncogenes can give rise to neoplastic transformation through protein-protein interactions.

BACKGROUND OF THE INVENTION

The yeast two-hybrid (Y2H) assay is a method for detecting protein-protein interactions using a genetic system. The technique may be used for charting protein interactions, and hence, identifying potential partners in genetic pathways. The assay is sensitive and yields the DNA sequences encoding proteins that interact. In a typical two-hybrid assay, a known protein that forms part of a DNA-binding domain hybrid is assayed against a library of all possible proteins present as transcriptional activation domain hybrids. Some two hybrid approaches rely on interaction mating. In this method, the protein fused to the DNA-binding domain and the protein fused to the activation domain are expressed in two different haploid yeast strains of opposite mating type and the strains are mated to determine if the two proteins interact. When haploid yeast strains of opposite mating type come into contact, mating occurs and results in fusion of the two haploids to form a diploid yeast strain. An interaction can thus be determined by measuring activation of a two-hybrid reporter gene in the dipoid strain.

WO 94/10300 and U.S. Pat. No. 5,283,173 describe methods for detecting the interaction between proteins using reconstitution of the activity of a transcriptional activator. This reconstitution makes use of chimeric genes which express hybrid proteins. The first hybrid contains the DNA-binding domain of a transcriptional activator fused to a known protein (the "bait"), with the DNA binding domain DNA binding element placed upstream of a reporter gene. "Prey" proteins are cloned as either random sequences or cDNAs and are fused to the amino- or carboxy-terminus of a transcription activation domain. If the bait and prey proteins are able to interact, they bring into close proximity the two domains of the transcriptional activator. This proximity is sufficient to cause transcription, which can be detected by the activity of a reporter gene that contains a binding site for the DNA-binding domain.

The disadvantages of these techniques is that irrelevant interactions with yeast proteins are generated. These include false-positive interactions that are unlikely to be found in living cells, and false-negative interactions, that is, those interactions that would otherwise be detected but are not. The techniques as disclosed in WO 94/10300 and U.S. Pat. No. 5,283,173 require the use of mating in solid medium which is cumbersome, labor-intensive, and does not preserve diploid cells for further analysis.

We have developed the mating strategy of the yeast two-hybrid assay into an automated format which allows many bait proteins to be processed. The format uses an arraying means, for example, microtiter plates and liquid mass-mating of a subset of a large, complex library. By tracking positive interactions in the library, we have also developed a method to create a functionally-subtracted library, that is, one that can be made devoid of a scorable phenotype. For example, our method allows for the determination of detection of hybrids that react promiscuously with many targets, such as heat shock proteins, and their elimination from any future considerations.

SUMMARY OF THE INVENTION

In accordance with the present invention there is provided a method for detecting protein-protein interactions comprising liquid mass-mating of subsets of a large, complex library. The method provides a means for subtracting irrelevant protein-protein interactions to yield a "functionally-subtracted" assay.

DETAILED DESCRIPTION OF THE INVENTION

According to an aspect of the present invention, there is provided a method for detecting an interaction between a first test protein and a second test protein, comprising:

(a) providing a host cell containing a reporter gene wherein the reporter gene expresses a detectable protein when the reporter gene is activated by an amino acid sequence including a transcriptional activation domain when the transcriptional activation domain is in sufficient proximity to the reporter gene;

(b) providing a first chimeric gene that is capable of being expressed in the host cell, the first chimeric gene comprising a DNA sequence that encodes a first hybrid protein, the first hybrid protein comprising:
  (i) a DNA-binding domain that recognizes a binding site on the reporter gene in the host cell; and
  (ii) a first test protein or fragment thereof that is to be tested for interaction with at least one second test protein or fragment thereof;

(c) providing a second chimeric gene that is capable of being expressed in the host cell, the second chimeric gene comprising a DNA sequence that encodes a second hybrid protein, the second hybrid protein comprising:
  (i) the transcriptional activation domain; and
  (ii) a second test protein or fragment thereof that is to be tested for interaction between the first test protein or fragment thereof; wherein interaction between the first test protein and the second test protein in the host cell causes the transcriptional activation domain to activate transcription of the reporter gene;

(d) introducing the second chimeric gene into the host cell and subsequently introducing said cells into an arraying means thereby creating a master library plate;

(e) introducing cells from the master library plate into a second arraying means thereby creating a mating set;

(f) introducing the first chimeric gene into the host cell and subsequently introducing said cell into the mating set;

(g) selecting for outgrowth of the interaction of the first and second genes;

(h) removing a portion of the mating set to a third arraying means thereby creating a rescue set;

(i) determining whether the reporter gene has been expressed in the mating set; and (j) analyzing the cells from the rescue plate.

The term "reporter gene" or "marker gene" as used herein means any gene whose expression may be assayed. More than one reporter gene may be encoded by the host cell in step (a) above.

The term "arraying means" as used herein means any method for holding clones in liquid media, suspension, or solid media, for example, microtiter plates or test tubes.

The term "selecting for outgrowth" as used herein means any method using a selectable means to either amplify or isolate a set of interacting proteins. This selectable means may include outgrowth in a nutritionally-deficient growth medium wherein the interacting proteins cause transcription of a biosynthetic gene or pathway. Examples of other useful selectable means include amino acid, metabolic, catabolic and nucleic acid biosynthetic genes, such as yeast HIS3, URA3, and LYS2, GAL1, E. coli galK, and CAT, GUS, antibiotic resistance, and any gene encoding a cell surface antigen for which antibodies are available. Outgrowth may be allowed to proceed for 5–10 days prior to selecting for outgrowth.

The term "analyzing" as used herein means any method for obtaining information regarding protein-protein interactions, for example, selecting positive clones, performing PCR, DNA sequence analysis, and comparison with databases such as LifeSeq® (Incyte Pharmaceuticals) or Genbank.

The term "functionally substracted" means devoid of a detectable phenotype that represents an irrelevant protein-protein interaction.

In a further aspect of the invention, determination of reporter gene expression and analysis of cells may be accomplished in one step, that is steps (i) and (j) above may be combined. Alternatively, steps (h), (i), and (j) may be eliminated.

A eukaryotic host strain, for example, a yeast strain, may be engineered to express the protein (the "bait") of therapeutic or diagnostic interest as a fusion protein covalently bonded to a known DNA binding domain of a transcriptional activator. The eukaryotic host strain also contains one or more "reporter genes", that is genes whose transcription is detected in response to a bait-prey interaction. Bait proteins, via their DNA binding domain, bind to their specific DNA site upstream of a reporter gene; reporter gene transcription is not stimulated, however, because the bait protein lacks its own activation domain.

To isolate genes encoding novel interacting proteins, cells of this strain containing a reporter gene and expressing a bait protein are transformed with individual members of a DNA (for example, a cDNA) expression library. Each member of the library directs the synthesis of a candidate interacting protein fused to a weak and invariant gene activation domain tag. The library-encoded proteins ("prey" proteins) that physically interact with the promoter-bound bait protein detectably activate the transcription of the downstream reporter gene and provide a ready assay for identifying particular cells which harbor a DNA clone encoding an interacting protein of interest.

In one embodiment, a cDNA library, created in E. coli, and comprising cDNA fused to the DNA sequence encoding the activation domain of the transcriptional activator, GAL4 protein, is plated onto 960 LB agar plates at a density of 1000 clones per plate. The E. coli colonies on each plate are pooled, plasmid DNAs are isolated, and the DNAs are used to transform yeast. The transformed yeast are plated onto solid medium and the colonies on each plate are pooled and aliquoted to separate wells of a 96-well microtiter plate to create an arrayed set of 10 "master library" plates. Five microliters from each well of the master library set is re-aliquoted to create a "mating set" and 5 μl of bait-containing yeast is then added separately to each well. The "bait" comprises a chimeric gene that expresses a hybrid protein containing the DNA-binding domain of GAL4 fused to a known protein. The host yeast strain contains the GAL1-lac-Z gene, which is able to bind the GAL4 DNA-binding domain. The GAL1-lacZ gene contains the E. coli lacZ gene encoding β-galactosidase. The activity of β-galactosidase is a measure of GAL4 function. Growth of yeast on galactose requires the transcription of genes regulated by GAL4 and is also a measure of GAL4 function. The liquid mass-mating is allowed to proceed for a period of time and the mating mixture is diluted 100 fold with leucine drop-out medium. After outgrowth of positively-interacting mated yeast diploids in the drop-out medium, a portion is removed to a separate set of "rescue" plates and a βGal analysis is performed on the mating set. Transcriptional activation can be determined by measuring β-galactosidase activity on galactose containing media. Wells containing any βGal activity are identified and clones from the corresponding set of wells from the rescue plates are analyzed by PCR sequencing.

In another aspect of the invention, there is provided a method for producing a functionally subtracted master library. Irrelevant protein-protein interactions may be eliminated by recombining only productive clones to the master library, thereby eliminating clones that produce proteins that are known to interact with many other proteins, for example heat shock-proteins.

In another further aspect of the present invention, there is provided a method for an open reading frame cloning strategy that involves the dynamic recoding of the ends of DNA molecules. This cloning strategy increases the efficiency of the assay by eliminating from analysis all clones that encode proteins that are out of frame with respect to the activation domain.

In dynamic recoding of an activation domain, the 3' end of the activation domain gene may be recoded to incorporate an amino acid hybrid peptide that also encodes the DNA controlling elements necessary for E. coli gene expression. In one aspect, these controlling elements comprise, in series; i) a sequence, for example, -35 and a -10 sequence, which acts as an E. coli promoter to initiate mRNA transcription, ii) a ribosome binding site and an ATG fMet codon necessary to initiate protein translation, iii) a multiple cloning site composed of one or more restriction sites which are preferably unique to the cloning vector, into which to clone stuffer fragments of DNA that can encode protein fusions to the activation domain, and iv) a reporter gene, for example, the lacZ gene, cloned out-of frame with respect to the ATG codon. In the open reading frame cloning system, the ATG may be in-frame with respect to the activation domain, the ATG may be out-of-frame with respect to the lacZ gene, there is a neglegible amount of βGal protein produced by the host cell in the absence of a stuffer fragment that restores the lacZ gene reading frame, and there is an absence of termination codons the end of the activation domain gene and the ATG codon.

The term "stuffer fragments" means any fragment of DNA generated synthetically, or through use of a method generally used to generate random or 3'-end primed cDNA molecules that can be cloned into the multiple cloning site of the above open reading frame cloning system.

In one aspect, random primed cDNA used as stuffer fragments may be sized-selected by agarose or polyacrylamide gel electrophoresis. Individual cDNA sized-selected by gel electrophoresis or other means may contain fragments which when cloned into the vector system described may be in one of six reading frames (3 reading frames in both forward and reverse orientation).

The recoded activation domain may be used in conjunction with the out-of-frame reporter gene to select for clones that restore the reading frame of the reporter gene. For example, if the lacZ gene is initially out-of-frame with respect to the ATG start of the recoded portion of the activation domain, then clones that restore the reading frame between that ATG and the lacZ gene will create protein fusions of that clone to the lacZ gene product. Fusions that restore βgal activity may be selected for chromogenically by using well-known dyes (e.g., Xgal) or on selective growth media containing lactose as the sole carbon source.

In a further aspect of the open reading frame cloning system, an *E. coli* suppressible termination codon (for example a TAG amber termination codon) may be encoded between the stuffer fragment and the reporter gene such that in phenotypically suppressing *E. coli* host strains the stop codon is suppressed by a suppressing tRNA molecule that inserts a specific amino acid. In non-suppressing host cells in which the interaction assay is performed the termination of protein translation would occur at the termination codon. The advantage to having this suppressible system is that the open reading frame reporter protein will not be fused to the carboxyl terminus of the encoded stuffer fragment-activation domain hybrid protein.

In another aspect of the invention there is provided the method according to steps (a) through (g) above or (a) through (i) above in the form of a kit for rapid screening.

The host cell may be any type of cell, including yeast, bacterial, or mammalian cell. The preferred host cell is a yeast cell, advantageously *Saccharomyces cerevisiae*.

The bait protein may be derived from a bacterial protein, a viral protein, an oncogene-encoded protein, a growth factor or an enzyme. Bait proteins may be chosen from any protein of known or suspected diagnostic or therapeutic importance. Preferred bait proteins include oncoproteins (such as myc, ras, src, fos) or any other proteins involved in cell cycle regulation (such as kinases, phosphatases).

Prey proteins may be encoded on a library of plasmids containing DNA inserts that are derived from genomic DNA, cDNA, or synthetically generated DNA sequences fused to the DNA sequence encoding the second amino acid domain. cDNAs may be constructed from any mRNA population and inserted into an equivalent expression vector. Such a library of choice may be constructed de novo using commercially available kits (for example, from Stratagene, La Jolla, Calif.) or using well established preparative procedures (for example, Current Protocols in Molecular Biology, New York, John Wiley & Sons, 1987). Alternatively, a commercially available cDNA library may be used. A prey protein may be encoded by a synthetic sequence or may be the product of a randomly generated open reading frame or a portion thereof.

Any suitable reporter gene may be used, for example, LEU2 gene or the lacZ gene. Examples of other useful genes whose transcription can be detected include amino acid and nucleic acid biosynthetic genes, such as yeast HIS3, URA3, and LYS2, GAL1, *E. coli* galK, and CAT, GUS, antibiotic resistance, and any gene encoding a cell surface antigen for which antibodies are available.

Those skilled in the art will also recognize that the reporter gene, DNA binding domain, and gene activation domain components may be derived from any appropriate eukaryotic or prokaryotic cell genomes or cDNAs as well as artificial sequences. Moreover, although yeast represents a preferred host organism, other host organisms such as mammalian cells may also be utilized.

Plasmid constructs, transformation, transfection, cell culture and detection of transcription may be performed by any method known in the art, for example, U.S. Pat. No. 5,283,173 and WO 94/10300, incorporated herein by reference hereto.

Any means for introducing genes into host cells may be used, for example, electroporation, transfection, transformation, or mating.

Advantages of the described invention include increased efficiency through elimination from further analysis of promiscuous proteins in arrayed libraries, creation of a means to functionally subtract classes of proteins from libraries, elimination from further analysis of clones not in a sepcified reading frame, reduced labor over current methods, re-use of primary libraries from arrayed master library sets, and accumulated knowledge over time of the make-up of the arrayed clones.

The invention may be illustrated by the following non-limiting examples.

EXAMPLE 1

Liquid Mass-mating, Functionally-subtracted Yeast Two-hybrid Assay

Restriction and DNA modification enzymes were purchased from various manufacturer's and used according to their recommendations.

Creation of arrayed cDNA libraries. *E. coli* cDNA libraries were purchased from Invitrogen and were plated at a low density (approximately 1000 clones per plate) onto LB+Amp plates and incubated 1–2 days at 37° C. Next, 3–4 ml of LB (containing 15% glycerol) was added to each plate, the plate rocked on a platform shaker at low speed, and the LB harvested after resuspension of the colonies in the LB was apparent. A 200 µl portion of the resuspended cells was removed for plasmid DNA isolation and the remaining cells frozen for long-term archival storage at −80° C.

Plasmid DNA was isolated by means of a kit obtained from Qiagen. Two hundred fifty (250) µl of P2 solution (Qiagen) was added to the 200 µl portion of cells in a 2 ml Eppendorf centrifuge tube. The two solutions were mixed gently and then 250 µl P3 solution (Qiagen) was added and the tube shaken. The mixture was then centrifuged at high speed (14,000 rpm) in an Eppendorf centrifuge. The clarified supernatent (500 µl) was pipetted to a new Eppendorf centrifuge tube and 1 ml of ethanol added to precipitate the DNA. The precipitated DNA was pelleted at high speed (14,000 rpm) for 15 minutes, the ethanol solution decanted off, and the pellet dried in vacuo. The pellet was resuspended in 50 µl distilled H2O and used directly to transform the yeast.

Yeast were transformed using the EZ Yeast Transformation kit (Zymo Research) according to the manufacturer's recommendation, using 2.5 µl DNA, 25 µl competent yeast strain EGY48 and 250 µl of EZ3. The transformed yeast were incubated for 1 hr at 30° C. and the total plated onto SD −trp agar plates. The plates were incubated for an additional 3–4 days at 30° C., and the cells harvested as for *E. coli* using 3–4 ml SD −trp+15% glycerol. The harvested yeast from each plate were separately aliquoted into different wells of a deep-dish 96-well plates (the "master library" plates) and frozen at −80° C. for long-term storage.

Yeast liquid-mating. Five µl from each of the yeast Master Library well was inoculated into 100 µl of SD −trp in a 96-well plate and grown overnight at 30° C. Five µl of each well were transferred to a new 96 well "mating" plate. A 5 µl aliquot of a bait culture ($OD_{600}$=1.0) was added to each well along with 10 µl YPD medium. The mating plates were placed into a resealable plastic bag and incubated for 12–36 hr at 30° C. Each well was then twice serially-diluted 10-fold (final 100 fold dilution) using S-min (−leu, −his, −trp, −ura, +gal, +raff) to a final volume of 110 µl. The diluted matings were incubated for an additional 5–10 days at 30° C. Ten µl of the mated wells were then transferred to a second set of plates prior to performing the µGal analysis (these mated and out-grown 10 µl stocks ("rescue plates") were later used for rescuing positive clones).

βGal Assay. Cells were lysed by the addition of 100 µl of a solution of Z buffer [$Na_2HPO_4$, (16.1 g $l^{31\ 1}$), $NaH_2PO_4$, (5.5 g $l^{-1}$), KCl (0.75 g $l^{-1}$), and $MgSO_4$, (0.25 g $l^{-1}$), adjusted to pH 7.0 and sterile-autoclaved] containing oxalyticase (100 U $ml^{-1}$), SDS (0.1%), and CPRG substrate (2 mg $ml^{-1}$). The plates were incubated at room temperature until the red βGal chromogenic substrate developed (usually 10 min to 2 hr). To quantitatively measure the wells it was necessary to remove the cell debris by either centrifugation or filtration. The CPRG substrate may be measured at an absorbance of 575 angstrom.

Test of pooling sensitivity. A test of the pooled liquid mating strategy was performed using the known strong Y2H interactors RPB4 (yeast polII subunit) and RPB7 (yeast polII subunit) as controls. The RPB4 subunit was subcloned into the activation-domain vector pJG4.5. The recombinant RPB4 fusion was subcloned into the DNA binding domain vector pEG202, transformed into the prey strain and mixed at various percentages (from 0 to 100%) with the same prey strain containing the pJG4.5 parental vector.

Figure 1:
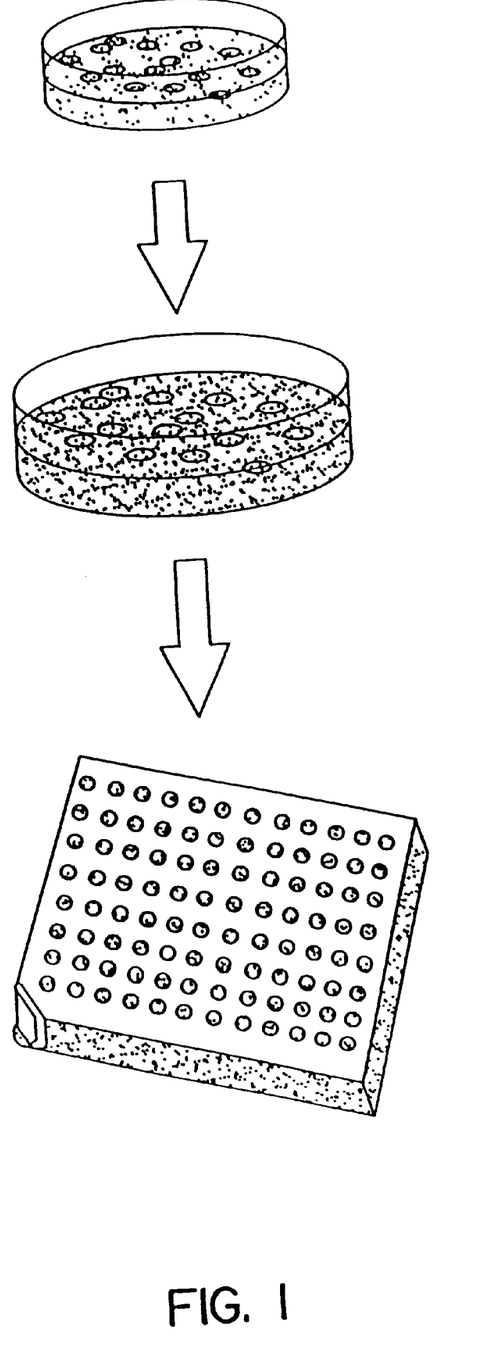
FIG. 1. Creation of arrayed cDNA libraries. *E. coli* EDNA libraries were plated at a low density (approximately 1000 colonies per plate) onto LB+Amp. Next, 3–4 ml of LB (containing 15% glycerol) was added to each plate and the LB harvested after resuspension of the colonies in the LB was apparent. Plasmid DNA was isolated by means of a kit obtained from Qiagen (Valencia, Calif.) and used directly to transform the yeast. The transformed yeast were plated onto SD −trp agar plates. The plates were incubated, and the cells harvested as for *E. coli* using 3–4 ml SD −trp+15% glycerol. The harvested yeast from each plate were separately aliquoted into different wells of deep-dish 96-well plates (the "master library" plates) and frozen at −80° C. for long-term storage.
Figure 2:
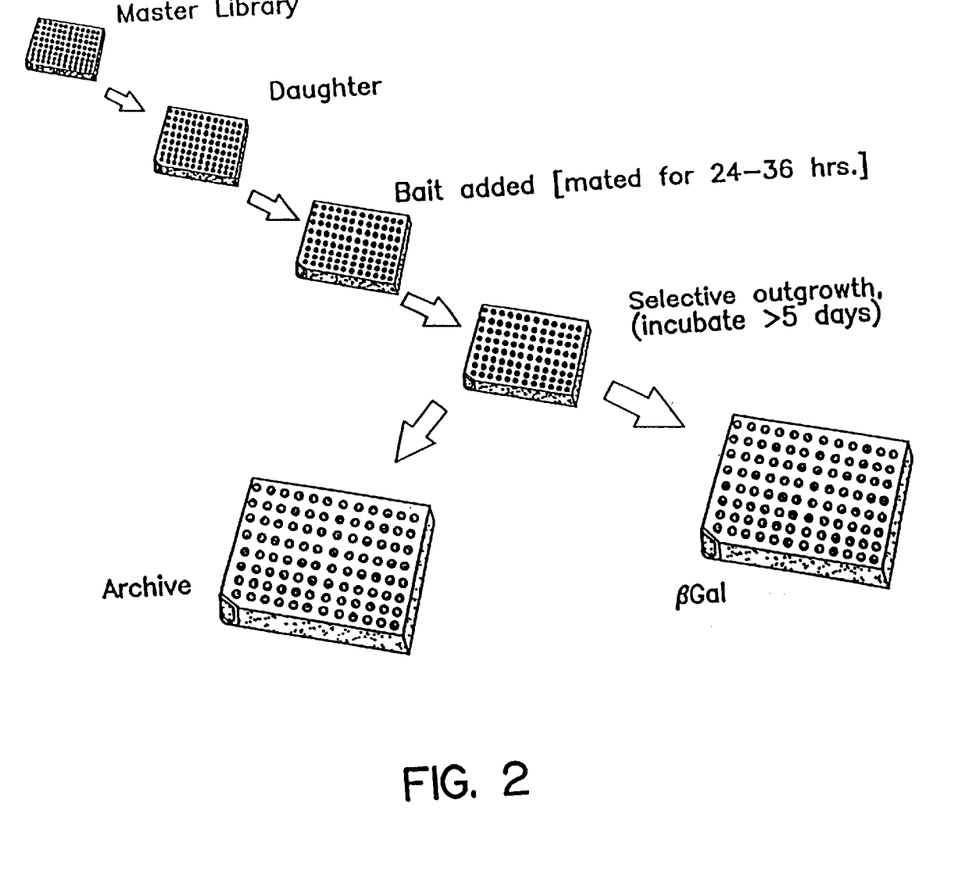
FIG. 2. Automatable Y2H format. The following steps were used to perform a Y2H analysis in a microtiter plate: i) Add bait strain to cDNA library strain in a well, ii) allow mating to occur in complex medium, iii) dilute mated mixture into minimal drop-out medium (−leu), iv) allow growth of positively-interacting proteins (growth as readout), v) Perform βGal assays (quantitative readout), vi) sequence (+) clones, query database(s).
Figure 3A:
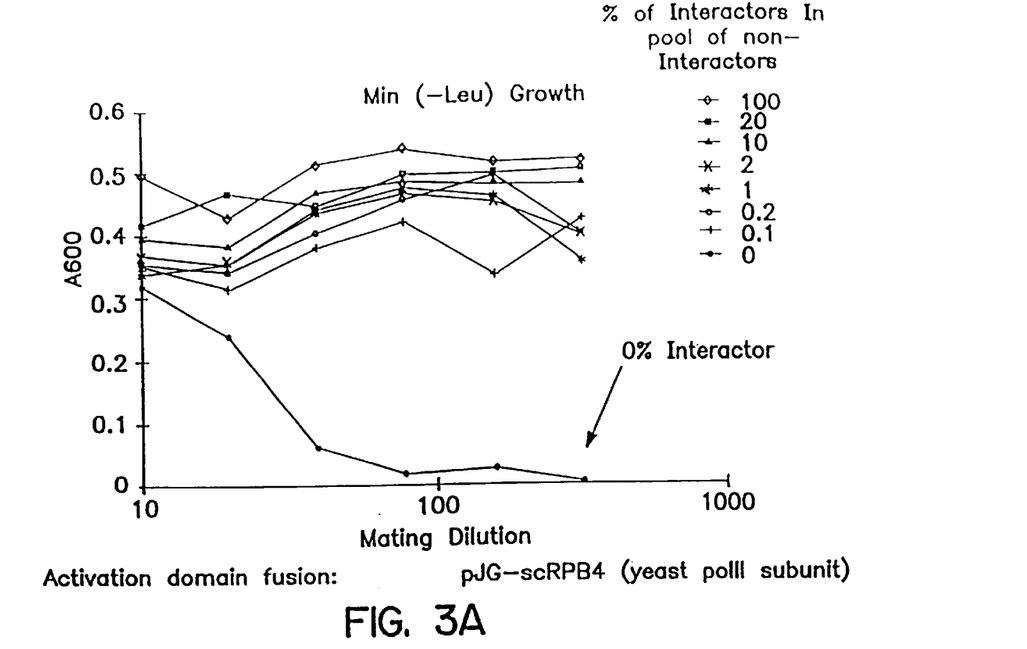
FIG. 3. Test of reporter activation in a pooled microtiter plate well. Known interactors were mixed at a known ratio and tested in the liquid mating format against a bait fusion. Top: selective outgrowth after dilution of mated yeast in leucine dropout medium. Bottom: βgal assay of wells.
Figure 3B:
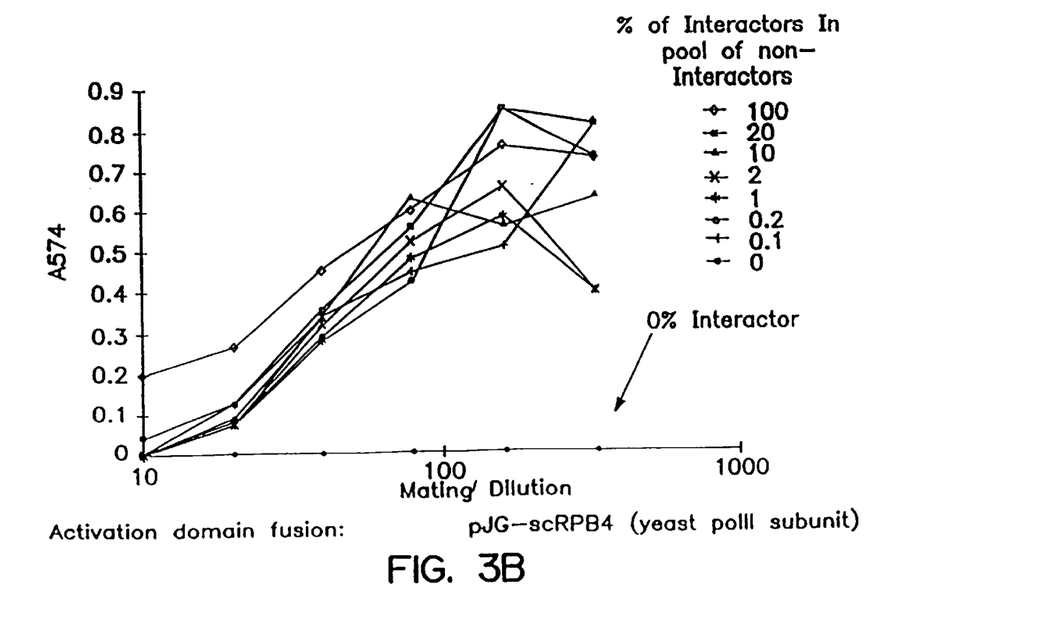

The results (shown in FIG. 2) demonstrated that we were able to recover prey strain for this interaction even when the prey initially represented approximately 0.1% of the prey "mating mixture." The results suggested that dilution of the complex YPD medium approximately 100-fold may be needed in order to see differential growth of the positively-interacting pairs. Dilution of the samples to lower the concentration of YPD complex may be preferable to other methods, such as centrifugation or filtration. This is because dilution is cheaper, faster, and easier to automate. The βGal analysis of the test of the reporter activation in a pooled microtiter plate format showed no significant difference between 0.1 and 100% recombinant fusion at the 100-fold dilution point. At higher dilutions scattering of the βGal activity occured. It may be that at the higher dilutions (of low percentage pools) sampling of positive interactors may be lost.

Test of pooled arrayed EDNA libraries. In the first test of the arrayed-cDNA library experiment, the nuclear receptors RXR and LXRa were tested against ca. $6 \times 10^5$ cDNAs in 6 microtiter plates. Most of the cDNAs were from the commercially-available cDNA libraries derived from human fetal liver (Invitrogen A202-01) and human fetal brain (Invitrogen A212-01).

Figure 4:
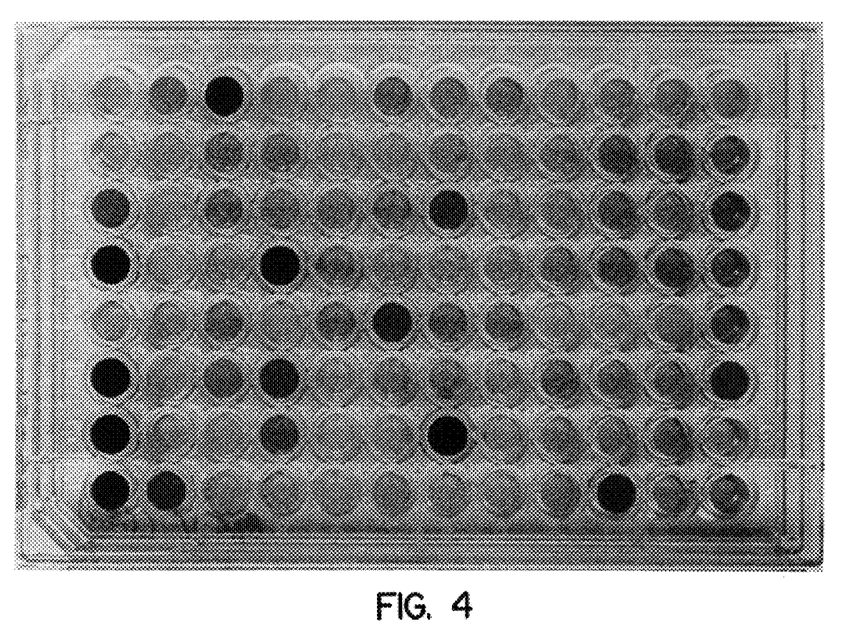
FIG. 4. Y2H analysis of the human Nuclear Receptor RXR screened against (approximately) $88 \times 10^4$ cDNA clones. Each well of the three 96-well plate shown represents a βgal assay performed on a pEG202 RXR bait plasmid-containing yeast strain mated to approximately 1000 yeast clones of a pJG4.5 AD library. The eight leftmost wells in each plate are positive and negative controls, (from top to bottom of the plate); a) pEG202×pJGRXR, b) pEG202, c) pEGKREV1×pJGRAF, d) pEGKREV1× pJGKRIT1, e) pEGRAS×pJGKRIT1, f) pEGRAS× pJGRAF, g) pEGRXR×pJGGOR4, and h) pEGGOR4× pJGRXR.

The cDNA-containing clones were seeded at approximately $1 \times 10^3$ clones per well. Briefly, the bait strain (containing the target protein, in this case either RXR or LXRa) was added to the cDNA library clones in the wells and mating was allowed to proceed in a complex medium. The mated mixtures were diluted into minimal medium (−leucine) and growth of interactors allowed to take place (growth indicating successful interaction) over 5 or more days. βGal assays were then performed on the wells (see example, FIG. 2), and clones from 10 wells exhibiting substantial βGal activity were re-isolated by streaking an aliquot of the library well onto solid minimal medium (−leucine). Plasmids were isolated from those clones and subjected to DNA sequence and bioinformatics analysis. The results are shown below in Table 1.

Some of the sequenced clones have been found through traditional Y2H analysis. These include TRIP6 (thyroid receptor interacting protein 6) which has been previously described in the literature from other "standard" interaction-trap experiments against other Nuclear Receptors (it had not yet been tested against LXRa) and TIF1. We believe these represent true-positives. The other clones, both encoding a GCN5 homolog, were isolated twice (in two different wells). We do not yet know if GCN5 homolog is a true or false positive.

Approximately a third of the interacting clones were found to have homology to cDNAs in the Incyte or GenBank databases, but have no ascribed function.

Several clones appear to be known promiscuous positives in interaction trap experiments (namely, cofilin and the heat shock proteins). Now that we know which wells these are in means that they can be eliminated from future analysis. However, it should be noted that when we do exclude these wells, we are also losing information in about the other clones in that well. For example, using RXR as a bait, we found an interaction with thymopoietin-related protein in well 1D9. Yet this same well, when querried with LXRa found a positive interaction with the promiscuous positive HSP90. It is hoped that a large enough library of cDNA is eventually used to obtain redundancy in the library analysis.

TABLE 1

Results of Y2H Analysis

| Bait | Sequence ID, well # | Representative Homology | Comments |
|---|---|---|---|
| RXR | 5rxr, 1A10 | TIF1 | known NR (+)[c] |
| LXRa | 13gor4, 3G4 | TRIP6 | known NR (+)[c] found in standard screen[e] |
| RXR | 1rxr, 1G6 | annexin (IPP) | found in standard screen[e] |
| LXRa | 7gor4, 5A10 | GCN5 homolog | involved in transcription[d] |
| LXRa | 20gor4, 5C5 | GCN5 homolog | involved in transcription |
| RXR | 3rxr, 1D9 | thymopoiten-related | plausable positive |
| LXRa | 12gor4, 2G1 | KIAA0229 | Genbank EST, (no known function) |
| LXRa | 5gor4, 1H8 | Incyte 3122030[b] | no annotation in GenBank, see also 21gor4 |
| LXRa | 9gor4, 2F8 | Incyte 004215[b] | no annotation in GenBank |
| LXRa | 15gor4, 4C2 | Incyte 1366945[b] | no annotation in GenBank |
| LXRa | 21gor4, 2B10 | Incyte 3122030[b] | no annotation in GenBank |
| RXR | 7rxr, 3B8 | nucleolin gene | known false (+)[a] |
| LXRa | 1gor4, 1A8 | huHSP86 | known false (+)[a] |
| LXRa | 3gor4, 1D9 | huHSP90 | known false (+)[a] |
| LXRa | 11gor4, 5E11 | cofilin | nvolved in cell structure, interacts with actin |

[a] known common positive in other Y2H screens (E. Golemis).
[b] No annotation found to genbank database-specific sequence.
[c] This protein is known to interact with several other nuclear receptors.
[d] GCN5 possesses histone acetyltransferase (HAT) activity.
[e] Protein was also isolated using traditional two-hybrid methodology.

EXAMPLE 2

Open Reading Frame Cloning Strategy

Figure 5A:
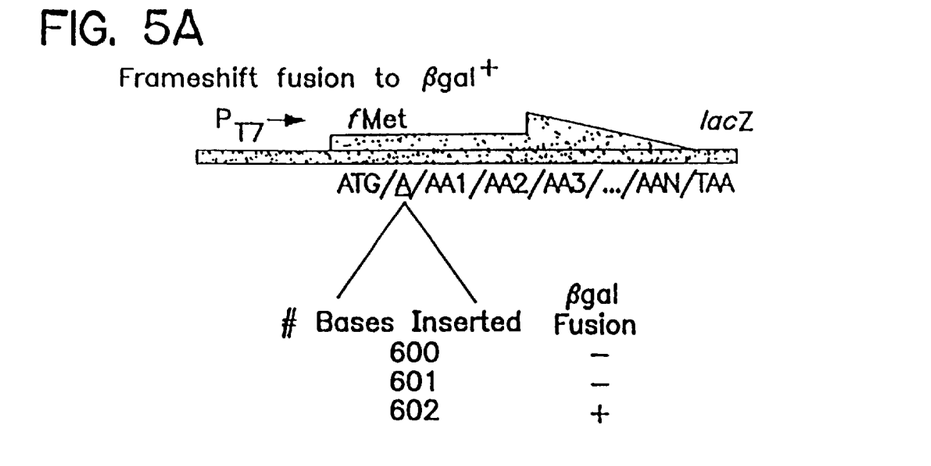
FIGS. 5A–5C. Open reading frame cloning strategy. Cloning Open Reading Frames. A. Frameshift fusion to βgal$^+$. Randomly sheared cDNA of approximately 600 base pairs were isolated and cloned into a frameshifted βgal gene. Transformed *E. coli* cells that became βgal$^+$ contained an open reading frame. B. Frameshift fusion to βgal$^+$ in a Sup$^+$ host. In a vector with an amber suppresible termination codon between the 3' end of the cDNA and the 5' end of βgal, the fusion of the cDNA to the βgal was controlled by the Sup phenotype of the *E. coli* strain. C. Frameshift fusion to M13gpIII in a Sup$^+$ host. The same type of cloning scheme may be adapted to fuse the 5' end of the M13 phage display protein to the cDNA, in this case viable phage will indicate successful cloning of the open reading frame.
Figure 5B:
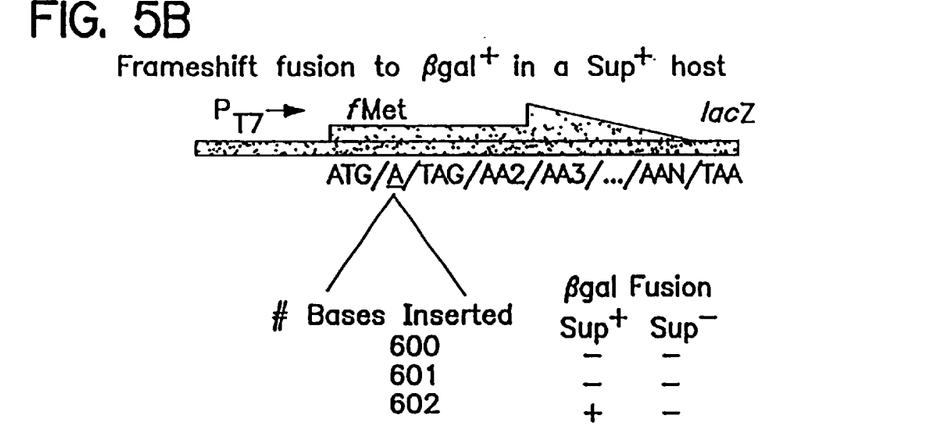
Figure 5C:
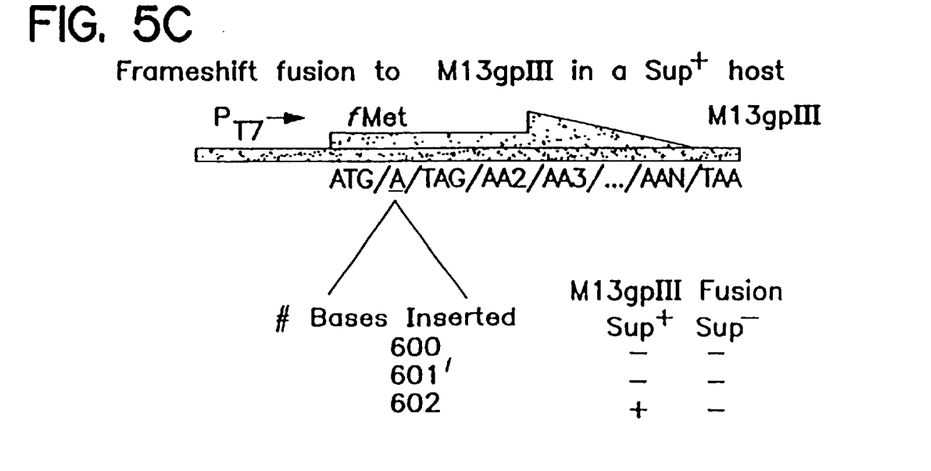

Cloning open reading frames and use of suppression to control 3' gene fusion. Randomly sheared cDNA of approximately 600 base pairs will be isolated and cloned into a frameshifted βgal gene (FIG. 5A). Transformed *E. coli* cells that become βgal+ will contain an open reading frame. In a vector with an amber suppresible termination codon between the 3' end of the cDNA and the 5' end of βgal, the fusion of the cDNA to the βgal can be controlled by the Sup phenotype of the *E. coli* strain (FIG. 5B). The same type of cloning scheme can be adapted to fuse the 5' end of the M13 phage display protein to the cDNA, in this case viable phage will indicate successful cloning of the open reading frame (FIG. 5C).

Figure 6:
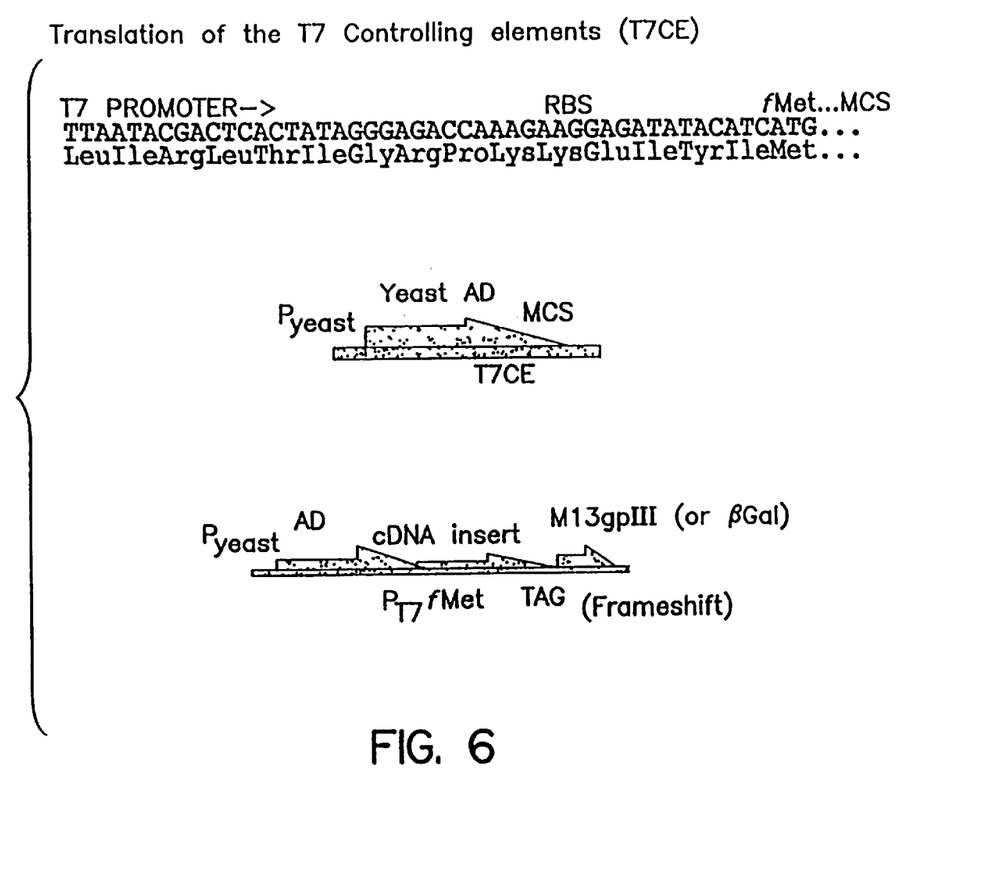
FIG. 6. Dynamic recoding of the 3' yeast activation domain. Translation of the T7 controlling elements (T7CE). The 3' end of the yeast activation domain (AD) was recoded to incorporate the controlling elements for *E. coli* gene expression. Shown is one example of recoding the controlling elements needed for bacteriophage T7 protein expression (SEQ ID NOS: 1 and 2). The recoded yeast activation domain was then used in conjunction with the open reading frame cloning system to fuse the correct reading frame to the activation domain, and simultaneously to a separate 3' fusion protein (for example, βgal or M13gp3).
Figure 7A:
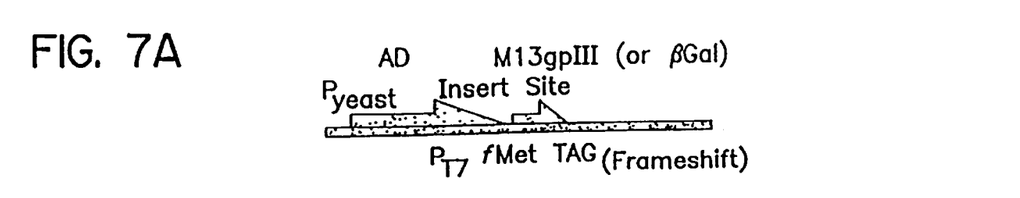
FIGS. 7A–7C. Phenotypic selection in *E. coli* of cDNA Open Reading Frames and concurrent fusion of them to the 3' end of the yeast activation domain (AD) and the 5' end of M13gpIII. A. clone random 500 bp cDNA fragments; transform T7RNAP$^+$, Sup$^+$ *E. coli*; screen plaques. B. Phage Display in *E. coli*. C. Yeast Two Hybrid in Yeast: transform T7RNAP$^-$, Sup$^+$ *E. coli*; transform M13 into Sup$^-$ yeast.
Figure 7B:
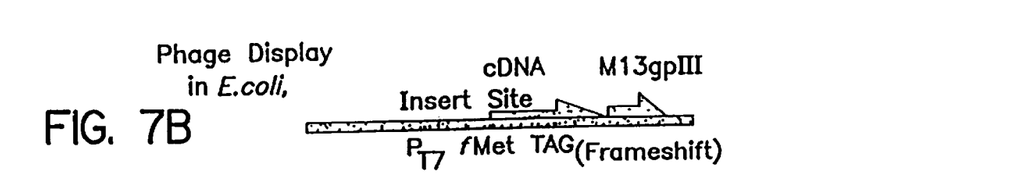
Figure 7C:
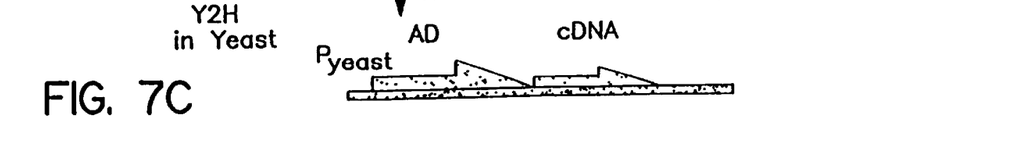

Dynamic recoding of the 3' end of the yeast activation domain. The 3' end of the yeast activation domain can be recoded to incorporate the controlling elements for *E. coli* gene expression. Shown in FIG. 6 is one example of recoding the controlling elements needed for bacteriophage T7 protein expression (SEQ ID NO:1); (SEQ ID NO:2). The recoded yeast activation domain can then be used in conjunction with the open reading frame cloning system to fuse the correct reading frame to the activation domain, and simultaneously to a separate 3' fusion protein (for example., βgal or M13gp3).

Phenotypic selection in *E. coli* of cDNA ORFs and concurrent fusion of them to the 3' end of the yeast activation domain and the 5' end of M13gpIII.

The application of which this description and claims form part may be used as a basis for priority in respect of any subsequent application. The claims of such subsequent application may be directed to any feature or combination of features described herein. They may take the form of product, composition, process or use claims and may include, by way of example and without limitation, one or more of the following claims.

What is claimed is:

1. A method for detecting an interaction between a first test protein and a second test protein, comprising:

(a) providing yeast or bacterial host cells of opposite mating type, one or both of which contain a reporter gene which expresses a detectable protein when the reporter gene is activated by an amino acid sequence including a transcriptional activation domain when the transcriptional activation domain is in sufficient proximity to the reporter gene;

(b) providing a first chimeric gene the first chimeric gene comprising a DNA sequence that encodes a first hybrid protein, the first hybrid protein comprising:
  (i) a DNA-binding domain that recognizes a binding site on the reporter gene in the host cell; and
  (ii) a first test protein or fragment thereof that is to be tested for interaction with at least one second test protein or fragment thereof;

(c) providing a second chimeric gene, the second chimeric gene comprising a DNA sequence that encodes a second hybrid protein, the second hybrid protein comprising:
  (i) the transcriptional activation domain; and
  (ii) a second test protein or fragment thereof that is to be tested for interaction with the first test protein or fragment thereof; wherein interaction between the first test protein and the second test protein in the host cell causes the transcription activation domain to activate transcription of the reporter gene;

(d) introducing the second chimeric gene into a host cell of a first mating type such that the second hybrid protein is expressed and subsequently introducing said cells into an arraying means thereby creating a master library plate;

(e) introducing cells from the master library plate into a second arraying means in liquid medium, thereby creating a mating set;

(f) introducing the first chimeric gene into a host cell of the opposite mating type of the host cell in step (d) such that the first hybrid protein is expressed and subsequently introducing said cell into the mating set, thereby allowing mating to occur in liquid medium;

(g) selecting for outgrowth of cells which express the reporter gene, thereby creating a selected mating set;

(h) removing a portion of the selected mating set to a third arraying means thereby creating a rescue set;

(i) determining whether the reporter gene has been expressed in cells in the selected mating set; and (j) analyzing cells from the rescue set which are the same as cells in the selected mating set in which the reporter gene is expressed, wherein detection of expression of the reporter gene in a cell is indicative of an interaction between the first test protein and the second test protein.

2. The method according to claim 1 wherein the reporter gene is selected from the group consisting of LEU2, lacZ, HIS3, URA3, LYS2, GAL1, E. coli galK, CAT, G418 and GUS.

3. The method of claim 1, wherein the yeast or bacterial cells contain two or more reporter genes.

4. A method for detecting an interaction between a first test protein and a second test protein, comprising:

(a) providing yeast or bacterial host cells of opposite mating type, one or both of which contain a reporter gene which expresses a detectable protein when the reporter gene is activated by an amino acid sequence including a transcriptional activation domain when the transcriptional activation domain is in sufficient proximity to the reporter gene;

(b) providing a first chimeric gene, the first chimeric gene comprising a DNA sequence that encodes a first hybrid protein, the first hybrid protein comprising:
  (i) a DNA-binding domain that recognizes a binding site on the reporter gene in the host cell; and
  (ii) a first test protein or fragment thereof that is to be tested for interaction with at least one second test protein or fragment thereof;

(c) providing a second chimeric gene, the second chimeric gene comprising a DNA sequence that encodes a second hybrid protein, the second hybrid protein comprising:
  (i) the transcriptional activation domain; and
  (ii) a second test protein or fragment thereof that is to be tested for interaction with the first test protein or fragment thereof; wherein interaction between the first test protein and the second test protein in the host cell causes the transcription activation domain to activate transcription of the reporter gene;

(d) introducing the second chimeric gene into a host cell of a first mating type such that the second hybrid protein is expressed and subsequently introducing said cells into an arraying means thereby creating a master library plate;

(e) introducing cells from the master library plate into a second arraying means in liquid medium, thereby creating a mating set;

(f) introducing the first chimeric gene into a host cell of the opposite mating type of the host cell in step (d) such that the first hybrid protein is expressed and subsequently introducing said cell into the mating set, thereby allowing mating to occur in liquid medium;

(g) selecting for outgrowth of cells which express the reporter gene, wherein expression of the reporter gene is indicative of an interaction between the first test protein and the second test protein in that cell.

5. The method of claim 4, wherein the yeast or bacterial cells contain two or more reporter genes.

6. A method for the selection of a test protein or fragment useful in the detection of protein-protein interactions, said method comprising:

(a) recoding a yeast activation domain gene, said recoding incorporating DNA controlling elements necessary for *E. coli* expression, said DNA controlling elements comprising (i) a sequence which acts as an *E. coli* promoter to initiate mRNA transcription;

(ii) a ribosome binding site and an ATG fMet codon necessary to initiate protein translation;

(iii) a cloning site composed of one or more restriction sites into which to clone stuffer fragments of DNA that can encode protein fusions to the activation domain; and (iv) a reporter gene, said reporter gene cloned out-of-frame with respect to the ATG codon;

(b) cloning stuffer fragments of DNA into the cloning site;

(c) fusing the stuffer fragments of DNA to the activation domain; and (d) separating clones that restore the reading frame of the reporter gene wherein a clone that restores the open reading frame is indicative of a test protein.

7. The method according to claim 6 wherein the reporter gene is selected from the group consisting of LEU2, lacZ, HIS3, URA3, LYS2, GAL1, *E. coli* galK, CAT, G418 and GUS.

8. The method of claim 6 wherein the reporter gene is lacZ.

9. The method of claim 6 wherein an *E. coli* suppressible termination codon is encoded between said stuffer fragment and said reporter gene such that in phenotypically suppressing *E. coli* host strains, the stop codon is suppressed by a suppressing tRNA molecule that inserts a specific amino acid.

10. The method of claim 9 wherein the *E. coli* suppressible termination codon is a TAG amber termination codon.

\* \* \* \* \*

SEQUENCE LISTING

<160> NUMBER OF SEQ ID NOS: 2

<210> SEQ ID NO 1
<211> LENGTH: 48
<212> TYPE: DNA
<213> ORGANISM: yeast
<220> FEATURE:
<221> NAME/KEY: CDS -continued

```
<222> LOCATION: (1)..(48)

<400> SEQUENCE: 1 tta ata cga ctc act ata ggg aga cca aag aag gag ata tac atc atg    48
Leu Ile Arg Leu Thr Ile Gly Arg Pro Lys Lys Glu Ile Tyr Ile Met
  1               5                  10                 15

<210> SEQ ID NO 2
<211> LENGTH: 16
<212> TYPE: PRT
<213> ORGANISM: yeast

<400> SEQUENCE: 2

Leu Ile Arg Leu Thr Ile Gly Arg Pro Lys Lys Glu Ile Tyr Ile Met
  1               5                  10                 15
```